United States Patent [19]

Hirai et al.

[11] Patent Number: 4,544,733
[45] Date of Patent: Oct. 1, 1985

[54] LATENT CURING AGENTS FOR EPOXY RESINS

[75] Inventors: Kiyomiki Hirai, Kawasaki; Koji Takeuchi, Yokohama; Masahiro Abe, Kawasaki; Nobuo Ito, Oisomachi, all of Japan

[73] Assignee: Ajinomoto Co., Inc., Tokyo, Japan

[21] Appl. No.: 673,989

[22] Filed: Nov. 21, 1984

[30] Foreign Application Priority Data

Nov. 21, 1983 [JP] Japan ................................. 58-219224

[51] Int. Cl.$^4$ .............................................. C08G 59/44
[52] U.S. Cl. ...................................... 528/123; 528/331; 564/149
[58] Field of Search ................... 528/123, 331; 564/149

[56] References Cited

U.S. PATENT DOCUMENTS

| | | | |
|---|---|---|---|
| 3,456,006 | 7/1969 | Aelony | 528/123 X |
| 3,467,707 | 9/1969 | Aelony | 528/123 X |
| 4,377,680 | 3/1983 | Sponseller et al. | 528/123 |
| 4,448,949 | 5/1984 | Ito et al. | 528/99 |
| 4,450,267 | 5/1984 | Ito et al. | 528/99 |

*Primary Examiner*—Earl Nielsen
*Attorney, Agent, or Firm*—Oblon, Fisher, Spivak, McClelland & Maier

[57] ABSTRACT

A latent curing agent for epoxy resin, characterized in that the latent curing agent is the hydrazides of the formula (I) or (II).

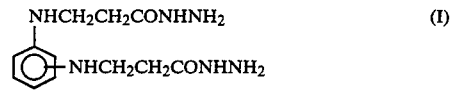

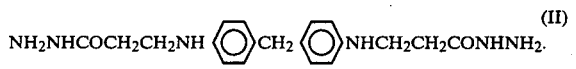

The present curing agent is useful in formulating storable, one-package, heat-curable epoxy resin-based compositions.

9 Claims, No Drawings

LATENT CURING AGENTS FOR EPOXY RESINS

BACKGROUND OF THE INVENTION

1. Field of the Invention

The present invention relates to a latent curing agent for epoxy curing resins. More particularly, it relates to a latent curing agent for epoxy resins which causes rapid resin curing at moderate, elevated temperatures and which gives epoxy resin compositions having excellent storage stability at room temperature.

2. Description of the Prior Art

Epoxy resins are widely employed as electric insulating materials, various moulded products, adhesives or coatings, because they give valuable cured resins having excellent mechanical, electrical and chemical properties when cured with suitable curing agents for example acid anhydride and amine curing agents. However, epoxy resin composition incorporating amine curing agents are cured rapidly at ordinary temperature and at elevated temperature and hence they lack storage stability. Also, epoxy resin composition incorporating acid anhydride curing agents are stable at ordinary temperature but heating for a long period of time at elevated temperature is required full curing. Usually, tertiary amines, quaternary ammonium compounds or organo metal complexes are further added to the composition for purpose of accelerating curing rate. However, the addition of such cure accelerator impairs storage stability markedly.

There have been eagerly desired so-called latent curing agents which are compatible with epoxy resins to form composition which is stable at relatively low temperature and which is rapidly cured when heated to elevated temperature. Representative compounds which have been heretofore proposed as latent curing agents are dicyandiamide, dibasic acid hydrazide, boron trifluorideamine adduct, guanamine and melamine. Among these compounds, dicyandiamide, dibasic acid hydrazide and guanamine are useful in formulating epoxy resin compositions having excellent storage stability but full curing by means of these compound could be achieved by heating at higher temperature than 150° C. for a long time. Also, boron trifluoride-amine adduct is hard to treat owing to its high hygroscopic property and it affects adversely upon the physical properties of the cured resin.

There has been heretofore known almost no latent epoxy curing agent which causes rapid curing at moderate elevated temperature, that is 100° C.–150° C. and which gives epoxy resin composition having excellent storage stability at ordinary temperature. The epoxy resin compositions which comprising the latent epoxy curing agent are so-called one pack-type epoxy resin.

One-pack type epoxy resins are preferable to the conventional two-pack type epoxy resins because the former cannot be misformulated and can be used continuously. A need therefore continues to exist for an improved curing agent for a one-pack type epoxy resin.

SUMMARY OF THE INVENTION

Accordingly, one object of the present invention is to provide a curing agent for a one-pack epoxy resin composition which effectively cures the resin at low temperatures and which provides for superior storage of the resin.

Briefly, these objects and other objects of the present invention as hereinafter will become more readily apparent can be attained by a curing agent for epoxy resins which is the hydrazides of the formula (I) or (II).

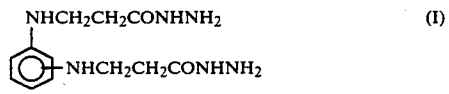

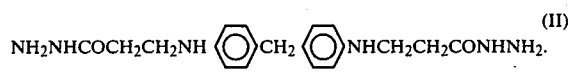

DETAILED DESCRIPTION OF THE PREFERRED EMBODIMENTS

An object of the present invention is to provide novel hydrazide-type curing agents which are useful in making storable one-package curable epoxy resin compositions.

Another object of the present invention is to provide hydrazide-type curing agents which alone or together with other curing agents can activate a rapid curing of epoxy resin composition at relatively low temperature and yet be extraordinarily resistant to gelling at 40° C. for more one month.

Further another object of the present invention is to provide hydrazide-type curing agents which give cured epoxy resin having excellent transparency and flexibility.

The above objects of the present invention may be substantially achieved by providing as curing agent hydrazide compound having the following general formulas (I) and (II).

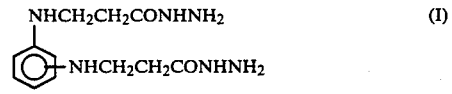

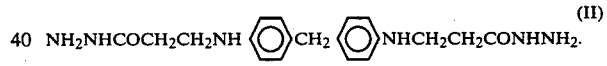

The hydrazides which may be represented by the above general formula (I) or (II) are novel compounds which are not disclosed in the literature and may be readily prepared by reacting adduct (A) of 1 mole of o-, m-, p-phenylenediamine and 2 moles or more moles of alkyl acrylate or adduct (B) of 1 mole of 4,4'-diaminodiphenyl-methane and 2 moles or more moles of alkyl acrylate, with hydrazine hydrate, said adduct of diamine and di- or more molecular alkyl acrylate.

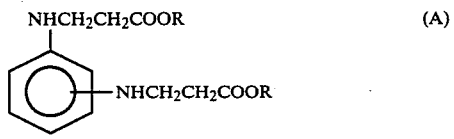

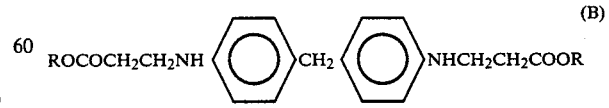

(where (A) is ortho-, meta- or para-isomer. R is alkyl group.)

The epoxy resin composition incorporating the prescribed amount of the hitherto known dibasic acid hydrazides, such as adipic acid hydrazide, sebacic acid hydrazide, isophthalic acid hydrazide and the like is cured when heated to 150° C. or higher temperatures. Contrary thereto, the epoxy resin composition incorporating prescribed amount of the hydrazides of the present invention has good storage stability and may be cured at 120° C. to 140° C. to give colorless, transparent and tough cured product.

The required amount of curing agent is determined by the number of active hydrogen atoms in the curing agent employed and the number of epoxy groups in the epoxy resins. In general, 0.5–1.5 preferably 0.7–1.2 active hydrogen equivalent weight per epoxy equivalent weight is employed.

As epoxy resins which may be applied to the hydrazide curing agents of the present invention, various well-known ones having an average of more than 1 epoxy groups in the molecule may be employed. Representative epoxy resins are those based on glycidyl ethers of polyhydric phenols especially glycidyl ether of Bisphenol A, glycidyl ether of Bisphenol F and glycidyl ether of phenolformaldehyde resin.

If necessary, other curing agents, cure accelerator and fillers may be added to the epoxy resin composition of the present invention.

The following examples illustrate the preparation of the hydrazides of the present invention, and usefulness of said hydrazides as latent epoxy curing agent.

EXAMPLE 1

Preparation of (I)′

$$\text{benzene ring with } NHCH_2CH_2CONHNH_2 \text{ (ortho positions)}$$

In the 300 ml of three-neck flask with the cooling and mixing apparatus, 21.6 g (0.2 mole) of o-phenylenediamine, 86 g (1 mole) of methyl acrylate, 40 ml of methanol and 2 ml of triethylamine were mixed. The mixture was heated for 5 hours with stirring. After cooling, reaction mixture was dissolved in 200 ml of benzene, washing with 100 ml of water three times, then benzene and excess methyl acrylate were removed under the reduced pressure to obtain 46 g of high viscous ester:

$$\text{benzene ring with } NHCH_2CH_2COOCH_3 \text{ (ortho)} \quad (A)'$$

46 g of obtained ester (0.16 mole) was dissolved in 100 ml of methanol. After adding 50 g of hydrazine hydrate (0.8 mole, 80% aqueous solution), the methanol solution was heated for 4 hours with stirring. The unreacted methanol hydrazine hydrate and methanol were removed under the reduced pressure. The residue was dissolved in 50 ml of methanol and allowed to stand overnight to precipitate the crystals. After filtration, the crystals were recrystallized from 50 ml of methanol, dried in vacuo to obtain 29 g of gray-brawnish prisms.

The analytical values were as shown below.
Melting point: 185°–186° C. Elemental analysis:

|  | C | H | N |
|---|---|---|---|
| Found (%) | 51.34 | 7.53 | 29.63 |
| Calc'd for $C_{12}H_{20}N_6O_2$ (%) | 51.41 | 7.19 | 29.98 |

EXAMPLE 2

Preparation of (I)″

$$NH_2NHCOCH_2CH_2NH-\text{benzene}-NHCH_2CH_2CONHNH_2$$

In the 300 ml of three-neck flask with the cooling and mixing apparatus, 21.6 g (0.2 mole) of p-phenylenediamine, 86 g (1 mole) of methyl acrylate, 40 ml of methanol and 2 ml of triethylamine were mixed. The mixture was heated for 5 hours with stirring. After cooling, reaction mixture was dissolved in 200 ml of benzene, washing with 100 ml of water three times, then benzene and excess methyl acrylate were removed under the reduced pressure to obtain 40.5 g of crystals:

$$CH_3OCOCH_2CH_2NH-\text{benzene}-NHCH_2CH_2COOCH_3 \quad (A)''$$

40.5 g of obtained ester (0.14 mole) was dissolved in 150 ml of methanol. After adding 50 g of hydrazine hydrate (0.8 mole, 80% aqueous solution), the methanol solution was heated for 4 hours with stirring. The unreacted hydrazine hydrate and methanol were removed under the reduced pressure. The residue was dissolved in 50 ml of methanol and allowed to stand overnight to precipitate the crystals. After filtration, the crystals were recrystallized from 50 ml of methanol, dried in vacuo to obtain 28 g of gray-brawnish prisms.

The analytical values were as shown below.
Melting point: 196°–198° C. Elemental analysis:

|  | C | H | N |
|---|---|---|---|
| Found (%) | 51.70 | 7.36 | 29.64 |
| Calc'd for $C_{12}H_{20}N_6O_2$ (%) | 51.41 | 7.19 | 29.98 |

EXAMPLE 3

Preparation of (I)‴

$$\text{benzene ring with } NHCH_2CH_2CONHNH_2 \text{ (meta positions)}$$

The product was obtained by the same procedure shown in example 2, without using m-phenylene-diamine in stead of p-phenylenediamine.

The analytical values were as shown below.
Melting point: 193°–195° C. Elemental enalysis:

|  | C | H | N |
|---|---|---|---|
| Found (%) | 51.59 | 7.60 | 29.64 |
| Calc'd for $C_{12}H_{20}N_6O_2$ (%) | 51.41 | 7.19 | 29.98 |

EXAMPLE 4

Preparation of NH$_2$NHCOCH$_2$CH$_2$NH 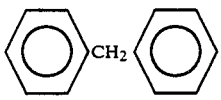 NHCH$_2$CH$_2$CONHNH$_2$ (II)

In the 300 ml of three-neck flask with the cooling and mixing apparatus, 19.8 g (0.1 mole) of 4,4'-diaminodiphenyl-methane, 43 g (0.5 mole) of methyl acrylate, 60 ml of methanol and 2 ml of triethylamine were mixed. The mixture was heated for 8 hours with stirring. After cooling, reaction mixture was dissolved in 200 ml of benzene, and washing with 100 ml of water three times, then benzene and excess methyl acrylate were removed under the reduced pressure to obtain 19 g of crystals:

CH$_3$OCOCH$_2$CH$_2$NH 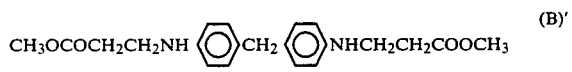 NHCH$_2$CH$_2$COOCH$_3$ (B)'

19 g of obtained ester (0.05 mole) was dissolved in 100 ml of methanol. After adding 19 g of hydrazine hydrate (0.3 mole, 80% aqueous solution), the methanol solution was heated for 4 hours with stirring. The unreacted hydrazine hydrate and methanol were removed under the reduced pressure. The residue was dissolved in 50 ml of methanol and allowed to stand overnight to precipitate the crystals. After filtration, the crystals were recrystallized from 50 ml of methanol, dried in vacuo to obtain 15 g of light-brawnish prisms.

The analytical values were as shown below.

Melting point: 175°–177° C. Elemental analysis:

|  | C | H | N |
|---|---|---|---|
| Found (%) | 61.01 | 7.38 | 22.09 |
| Calc'd for C$_{19}$H$_{26}$N$_6$O$_2$ (%) | 61.60 | 7.07 | 22.69 |

EXAMPLE 5

Reactivity and storage stability of the formulated epoxy resin composition were evaluated.

1. PREPARATION OF THE SAMPLE

The formulation of the sample is shown in Table 1. The individual components were sufficiently mixed in a mortar.

2. EVALUATION OF THE REACTIVITY (2-1) Onset temperature and peak temperature were measured by differential thermal analysis (DTA)

| Sample weight: | about 10 mg |
|---|---|
| Standard material: | α-Al$_2$O$_3$ |
| Heating rate: | 5° C./min. |

(2-2) The sample was put into a Geer's oven for 60 minutes and cured temperature was measured.

3. STORAGE STABILITY

The sample was put into a Geer's oven set to 40° C. and the day required for the sample becoming non-fluidity was measured.

4. GLASS TRANSITION POINT (TG)

The Tg of the cured sample at setting temperature was measured by the TMA penetration method using the thermal analytical aparatus (TMA, RIGAKU Electric Company).

The measure condition was as follows:

| Heating rate: | 10° C./min |
|---|---|
| Load: | 10 g |
| Diameter of the needle: | 1 mm∅ |

The results obtained are summarized in table 2.

TABLE 1

|  |  | Formulation No. | | | | | | | | |
|---|---|---|---|---|---|---|---|---|---|---|
|  |  | 1 | 2 | 3 | 4 | 5 | 6 | 7 | 8 | 9 |
| The present invention | Epon 828*[1] | 100 | 100 | 100 | 100 | 100 | 100 | 100 | 100 | 100 |
|  | Compound (1) | 37 | | | | | | | | |
|  | Compound (2) | | 37 | | | | | | | |
|  | Compound (3) | | | 37 | | | | | | |
|  | Compound (4) | | | | 49 | | | | | |
| Control | Adipic dihydrazide | | | | | | | 23 | | |
|  | Isophthalic dihydrazide | | | | | | | | 26 | |
|  | Dicyandiamide | | | | | | | | | 8 |

*[1]A product of Shell Chemical Co. bisphenol A type epoxy resin having epoxy equivalent of 175–120.

TABLE 2

|  |  | Item | | | | | |
|---|---|---|---|---|---|---|---|
|  |  | Reactivity | | | Storage | Tg (°C.) | |
|  | Formulation No. | Onset temp. (°C.) | Peak temp (°C.) | Cured temp. (°C.) (60 min) | stability (40° C.) | cured temp. (°C.) | curing hour (h) |
| The present invention | No. 1 | 134 | 169 | 130 | >2 weeks | 107<br>141 | (130–1)<br>(130–3) |
|  | No. 2 | 148 | 170 | 130 | " | 85<br>102 | (130–1)<br>(130–3) |
|  | No. 3 | 150 | 176 | 140 | " | 111<br>130 | (140–1)<br>(140–3) |

TABLE 2-continued

|  | Formulation No. | Reactivity Onset temp. (°C.) | Reactivity Peak temp (°C.) | Reactivity Cured temp. (°C.) (60 min) | Storage stability (40° C.) | Tg (°C.) cured temp. (°C.) | Tg (°C.) curing hour (h) |
|---|---|---|---|---|---|---|---|
|  | No. 4 | 134 | 164 | 120 | " | 160 | (140-1) |
|  |  |  |  |  |  | 160 | (140-1) |
| Control | No. 7 | 151 | 173 | 160 | " | 95 | (170-1) |
|  |  |  |  |  |  | 125 | (170-3) |
|  | No. 8 | 158 | 192 | 160 | " | 167 | (170-1) |
|  |  |  |  |  |  | 172 | (170-3) |
|  | No. 9 | 160 | 199 | 180 | (Partial separation occurred) | — | (170-1) |
|  |  |  |  |  |  | 113 | (170-3) |

The result of Table 2 shows that the latent curing agent for epoxy resin in this invention has excellent storage stability and reactivity. Especially, the reactivity of this agent is superior to the control agent.

What we claim is:

1. A compound having the formula (I) or (II):

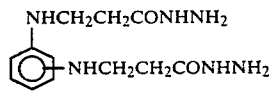
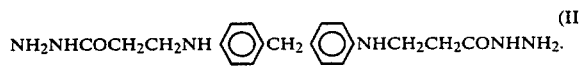

2. A compound claimed in claim 1, wherein (I) is at least one ortho-, meta- or para-isomer.

3. A curing agent suitable for use with epoxy resin compositions comprising a compound having the formula (I) or (II):

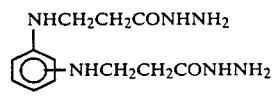
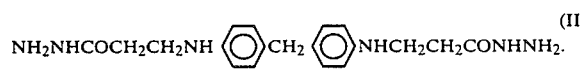

4. The curing agent claimed in claim 3, wherein (I) is at least one ortho-, meta- or para-isomer.

5. A curable epoxy resin composition comprising (a) an epoxy resin having an average of more than one epoxy group per molecule and (b), as curing agent, a compound having formula (I) or (II):

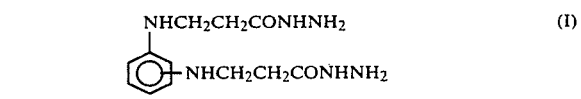
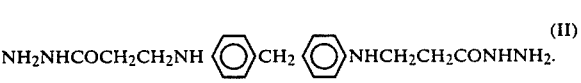

6. The curable epoxy resin composition claimed in claim 5, wherein the amount of said compound is enough to provide 0.5-1.5 times active hydrogen equivalent might based on epoxy equivalent weight.

7. The curable epoxy resin composition claimed in claim 5, wherein (I) at least one is ortho-, meta- or para-isomer.

8. The curable epoxy resin composition claimed in claim 5, wherein said epoxy resin is polyglycidyl ether of polyhydric phenol.

9. A cured resin obtained by contacting an epoxy resin having an average of more than 1 epoxy group per molecule with as curing agent a compound having the formula (I) or (II):

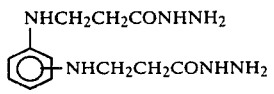
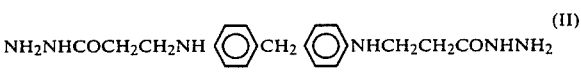

wherein (I) is at least one ortho-, meta- or para-isomer, the amount of said compound being enough to provide 0.5-1.5 times active hydrogen equivalent weight based on epoxy equivalent weight.

* * * * *